US005474072A

United States Patent [19]

Shmulewitz

[11] Patent Number: 5,474,072
[45] Date of Patent: Dec. 12, 1995

[54] METHODS AND APPARATUS FOR PERFORMING SONOMAMMOGRAPHY

[75] Inventor: Ascher Shmulewitz, Seattle, Wash.

[73] Assignee: NeoVision Corporation, Seattle, Wash.

[21] Appl. No.: 145,958

[22] Filed: Oct. 29, 1993

[51] Int. Cl.⁶ .................................. A61B 8/00; A61B 6/04
[52] U.S. Cl. ...................... 128/660.09; 128/915; 378/37; 378/208
[58] Field of Search ........................... 128/653.1, 660.01, 128/660.09, 660.08, 660.10, 661.01, 915; 378/37, 208

[56] References Cited

U.S. PATENT DOCUMENTS

| | | | |
|---|---|---|---|
| 3,765,403 | 10/1973 | Brenden | 128/2 V |
| 3,971,950 | 7/1976 | Evans et al. | 250/451 |
| 4,433,690 | 2/1984 | Green et al. | 128/660 |
| 4,434,799 | 3/1984 | Taenzer | 128/660 |
| 4,485,819 | 12/1984 | Igl | 128/660 |
| 4,599,738 | 7/1986 | Panetta et al. | 378/37 |
| 4,625,555 | 12/1986 | Fujii | 73/597 |
| 4,862,893 | 9/1989 | Martinelli | 128/662.03 |
| 4,966,152 | 10/1990 | Gang et al. | 128/661.07 |
| 5,007,428 | 4/1991 | Watmough | 128/660.04 |

FOREIGN PATENT DOCUMENTS

| | | | |
|---|---|---|---|
| 0105812 | 4/1984 | European Pat. Off. | A61B 10/00 |
| 3222053 | 12/1983 | Germany | A61B 10/00 |
| 3227624 | 1/1984 | Germany | A61B 10/00 |
| 3405537 | 8/1985 | Germany | A61B 8/00 |

OTHER PUBLICATIONS

Kossoff, G. et al "Apparatus for Ultrasonic Examination of Deformable Objects", PCT Publ. #WO8302053 Publ Jun. 1983.

B. D. Fornage, et al., "Breast Masses: US–Guided Fine Needle Aspiration Biopsy," Radiology, Feb., 1987, pp. 409–414.

I. Andersson, "Mammogaphy in Clinical Practice," Medical Radiography and Photography, vol. 62, No. 2. 1986 (Eastman Kodak Co.).

V. P. Jackson, "The Role of US in Breast Imaging," Radiology, Nov. 1990, pp. 303–311.

F. M. Hall, "Mammographic Second Opinions Prior to Biopsy of Nonpalpable Breast Lesions," Arch–Surg., Mar. 1990, pp. 298–299.

K. Dowlatshahi, et al. "Nonpalpable Breast Tumors: Diagnostic with Sterotaxic Localization and Fine Needle Aspiration," Radiology, Feb. 89, pp. 427–433.

R. F. Brem and O. M. B. Gatewood, "Template–guided Breast US," Radiology, Sep. 1992, pp. 872–874.

W. F. Conway et al., "Occult Breast Masses: Use of a Mammographic Localizing Grid for US Evaluation," Radiology, Oct. 1991, pp. 143–146.

E. B. Mendelson, "Ultrasound secures place in breast Ca management," Diagnostic Imaging, Apr. 1991, pp. 120–129.

S. H. Parker, et al. "US–guided Automated Large–Core Breast Biopsy," Radiology, May 1993, pp. 507–511.

E. Rubin, "Breast Cancer in the 90's," Applied Radiology, Mar. 1993, pp. 23–26.

G. Newstead, "When and when not to biopsy the breast," Diagnostic Imaging, Mar. 1993, pp. 111–116.

Primary Examiner—Francis Jaworski
Attorney, Agent, or Firm—Fish & Neave; Nicola A. Pisano

[57] ABSTRACT

Apparatus is provided that combines mammography equipment with an ultrasonic transducer to generate ultrasonic images of the internal structure of breast tissue that are in geometric registration with a mammogram. The apparatus includes a radiolucent and sonolucent compression plate, and in alternative embodiments, a gantry driven ultrasound transducer or a phased array ultrasonic transducer. Methods are also provided for generating a mammogram and a plurality of corresponding ultrasound images without moving the breast between the mammogram exposure and the ultrasound imaging.

23 Claims, 7 Drawing Sheets

METHODS AND APPARATUS FOR PERFORMING SONOMAMMOGRAPHY

This invention relates to methods and apparatus for imaging breast tissue employing both X-ray and ultrasound technology to provide enhanced diagnostic capability. In particular, the present invention provides methods and apparatus for augmenting conventional mammography equipment with an ultrasonic imaging system that provides geometrically registered X-ray and ultrasonic fields.

BACKGROUND OF THE INVENTION

The use of X-ray technology for providing two-dimensional images of breast tissue for diagnosis of carcinoma or other abnormalities is well known. X-ray imaging has a number of limitations which are universally recognized by radiologists. In particular, X-ray imaging of breast tissue has the inherent limitation that a mammogram provides only a two-dimensional image of a three-dimensional object. Thus, although a potential area of concern may be indicated on a mammogram, the elevation of the subject area within the breast may be uncertain, leading to a biopsy of broader scope than would otherwise be necessary.

In addition to conventional mammograms, apparatus has been developed that employs ultrasound technology for breast tissue imaging. Ultrasound imaging devices display echoes received from a piezoelectric transducer as brightness levels proportional to the backscattered echo amplitude. The brightness levels are displayed at the appropriate echo range and transducer position or orientation, resulting in cross-sectional images of the object in a plane perpendicular to the transducer emitting face.

Previously known ultrasound equipment, in the form of dedicated ultrasound breast imaging apparatus, have met with limited acceptance by the medical community. For example, Brenden U.S. Pat. No. 3,765,403 describes the use of ultrasound technology to provide direct and holographic imaging of breast tissue. That device requires the patient to lie prone on a patient supporting surface while her breast is immersed in a water-filled tank. Taenzer U.S. Pat. No. 4,434,799 describes an alternative device wherein the patient's breast is immobilized between an ultrasonic transducer and ultrasonic receiving transducer. Both of the systems described in those patents are dedicated ultrasound systems.

In addition to dedicated apparatus, hand-held ultrasound devices have found application in performing free-hand examinations. Free-hand examination using a hand-held ultrasound transducer is described, for example, Mendelson, "Ultrasound Secures Place In Breast Ca Management", *Diagnostic Imaging*, April 1991, pp. 120–129. A drawback of such freehand examinations, when used to supplement mammography, is the inability to provide geometric registration between the mammogram and ultrasound images. This lack of registration may result in the freehand ultrasound examination being directed at a different portion of the breast tissue than would otherwise have been indicated were geometric registration possible.

For example, recent studies have shown that over 10% of the masses detected with free-hand ultrasound and initially believed to be the mammographically detected mass, were subsequently found to represent different areas of the breast. Because ultrasound can depict 2–3 times more cysts than mammography, the possibility of characterizing a malignant lesion as benign is real.

In addition, the three dimensional shape of the lesions, as reported in Homer, "Imaging Features And Management Of Characteristically Benign And Probably Benign Lesions, *Rad. Clin. N. Am.*, 25:939–951 (1987) and the increased vascularity associated with carcinoma, as reported in Cosgrove et al., "Color Doppler Signals From Breast Tumors", *Radiology*, 176:175–180 (1990), have been suggested to be added to the diagnostic criteria. Such volumetric spatial registration of the ultrasonic data with a mammogram cannot be accomplished with previously known ultrasound devices.

While there is recognition within the medical community of the advantages offered by ultrasound technology, the construction of conventional mammography and sonography equipment has prevented combination of these two technologies. In particular, polycarbonates such as Lexan®, are typically used in mammography because of their tensile strength and transparency to X-ray. These materials are acoustically opaque.

On the other hand, the compression plates used in the conventional breast ultrasound devices, for example, Brenden U.S. Pat. No. 3,765,403, are composed of materials such as polystyrene or polyurethane, which have insufficient tensile strength for use in mammography equipment.

Because of their high densities, all of the materials potentially useful for the compression plates in mammography equipment have relatively high attenuation and reflection coefficients (table 1, below). These characteristics limit the use of ultrasound to low frequencies (3 MHz or below as described in Taenzer U.S. Pat. No. 4,434,799) and shallow depths. At 10 MHz and a 0.5 to 1 cm roundtrip path through a typical compression plate, the attenuation with most polymers would be 20–50 dB.

For any interface thicker than a quarter wavelength (several hundred microns, depending on the nominal frequency and acoustic velocity within the material) transmission loss must also be taken into account (which could exceed 50 dB). In addition, the impedance mismatch between the biological tissues, the compression plate and the transducer results in at least a 6 dB loss at each interface, or an additional total loss of 24 dB roundtrip. Since the total dynamic range is no greater than 100 dB for a typical ultrasound system, ultrasound imaging through previously known mammographic compression plates would be impossible.

In addition, since the acoustic propagation within the compression plate is substantially different than water or the coupling gel, refraction effects on each of the emitted waves from the elements of a phased array, would severely corrupt the beamforming process that assumes a constant velocity of 1540 m/sec.

TABLE 1

| Material | Attenuation Coefficient (dB/MHz/cm) | Impedance (Pa s/m) |
|---|---|---|
| Polyvinylchloride | 11.1 | 3.4 |
| Polybutane | 6.1 | 3.2 |
| Polyacetyl, Polyethylene, Polypropylene | 2.5–3.3 | 2.2 |
| Polyamid (Nylon) | 1.1 | 2.9 |
| Polystyrene | 1 | 2.5 |
| Water | 0.02 | 1.5 |

The lower frequencies used in the previously known ultrasonic devices would be inadequate for the diagnostic applications, which currently require 7–10 MHz transducers, yet this higher frequency requirement would increase the transmission loss by at least threefold (in dB). While it is possible to generate larger pulses in the transducer in the water bath approach, the low electro-mechanical efficiency results in heat generation. Placing the transducer directly upon the compression plate, and as a result in close proximity to the biological tissue, would require even higher energy pulses from each element. The resulting heat generation would cause damage and should be avoided.

Conway, "Occult Breast Masses: Use Of A Mammographic Localizing Grid For US Evaluation", *Radiology*, 181:143–146 (1991) and Brem and Gatewood, "Template Guided Breast Ultrasound", *Radiology*, 184:872–874 (1992), describe attempts to achieve spatial registration between a mammogram and an ultrasound image by cutting a hole in the compression plate of the mammography device to insert an ultrasound transducer. In Conway et al., a cut-open compression plate with a localization grid was used to allow acoustic transmission. Using the identical ultrasound device, the ultrasound study was performed in free-hand and through the localizing grid. Several additional X-ray exposures were needed to detect the lesion, replace the compression plate with the cut-out grid compression plate, then place the cut-out over the coordinates of the lesion. The grid positioned ultrasound detected 24% more lesions than free-hand. Ten percent were misidentified using free-hand ultrasound. None of the lesions were misidentified with the grid-guided compression.

The approach described in the foregoing articles has several practical drawbacks. For example, in Conway the patient's breast is marked with an indelible pen to assist the mammographer in repositioning the patient's breast on the localization grid after the compression plate is replaced by the cut-open compression plate used with the ultrasound transducer. As noted in that article, even the use of indelible markings on the patients skin does not absolutely guard against movement of the underlying breast tissue. In addition, the mammographer had to be present during the exam to ensure correct positioning, and the procedure length was significantly increased.

A cut-open compression plate with a localization grid suffers from the problem that the ultrasonic field is interrupted by the shadow of the compression plate, in all regions but the cut-out hole, thereby requiring prior knowledge of the interrogated lesion. As a result, in order to obtain a complete ultrasonic diagnostic image of the desired region of interest, it would be necessary to carry out a complex and burdensome manipulation of the mammographic compression procedure, and expose the patient to additional ionizing radiation.

In view of the drawbacks of previously known breast imaging apparatus and methods, it would be desirable to provide an apparatus and methods for providing geometrically registered X-ray and ultrasound images of breast tissue.

It would further be desirable to provide a compression plate that is both radiolucent and sonolucent, so that both a mammogram and ultrasound images of a patient's breast tissue may be obtained without moving the breast between the X-ray exposure and ultrasound imaging.

It also would be desirable to provide an apparatus for moving an ultrasound transducer through a predetermined path to generate a plurality of ultrasound images of breast tissue at preselected intervals.

It would be still further desirable to provide an apparatus capable of correlating geometrically registered X-ray and ultrasound images to provide holographic views of a patient's breast tissue.

SUMMARY OF THE INVENTION

In view of the foregoing, it is an object of the present invention to provide an apparatus and methods for providing geometrically registered X-ray and ultrasound images of breast tissue.

It is another object of the invention to provide a compression plate for use in combination mammography/ultrasound (hereinafter "sonomammography") apparatus that is both radiolucent and sonolucent, so that both a mammogram and ultrasound images of a patient's breast tissue may be obtained without moving the breast between the X-ray exposure and ultrasound imaging.

It is a further object of the present invention to provide an apparatus for contacting an ultrasound transducer to a compression plate for providing ultrasound images of breast tissue at preselected intervals.

It is a further object of the invention to provide radiolucent ultrasound transducer apparatus for use in sonomammography apparatus, to provide a plurality of ultrasound images of breast tissue that are in geometric registration with a mammogram obtained by the equipment.

It is a still further object of the invention to provide an apparatus capable of correlating geometrically registered X-ray and ultrasound images to provide holographic views of a patient's breast tissue.

These and other objects of the invention are accomplished in accordance with the principles of a first embodiment of the invention by providing a radiolucent and sonolucent compression plate that enables sonography apparatus to be combined with conventional mammography equipment. Either before or after the X-ray exposure, a carriage mounted ultrasound transducer is translated in increments across the compression plate to generate a plurality of sectional views of the breast tissue. The X-ray and ultrasound images produced by the sonomammography apparatus of the present invention are therefore in geometric registration. Those images may in turn be processed by a conventional microprocessor-based workstation to provide holographic views of the internal features of a patient's breast.

In a second embodiment of the present invention, a radiolucent ultrasound transducer is provided which is adapted to conventional mammography equipment. The transducer of the present invention, which may be a phased array, serves as both the sending and receiving ultrasound transducer, and is positioned beneath the diffraction grid typically found in mammography equipment for reducing exposure of the X-ray film by scattered radiation. The diffraction grid is modified to function as the component of the acoustic circuit in this embodiment.

In yet a third embodiment of the present invention, an ultrasound transducer is mounted on a movable carriage positioned between the compression plate and the diffraction grid of conventional mammography equipment. For this embodiment, neither the sonolucent compression plate of the first embodiment, nor the radiolucent ultrasound transducer of the second embodiment, is required.

The present invention also includes methods of imaging a patient's breast tissue using mammography and sonography equipment to provide geometrically registered images. The methods further include processing of those images using a conventional microprocessor based workstation to permit image-guided biopsy of the patient' tissue. Alternatively, the medical practitioner can perform detailed review of the processed and stored images in an off-line setting.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
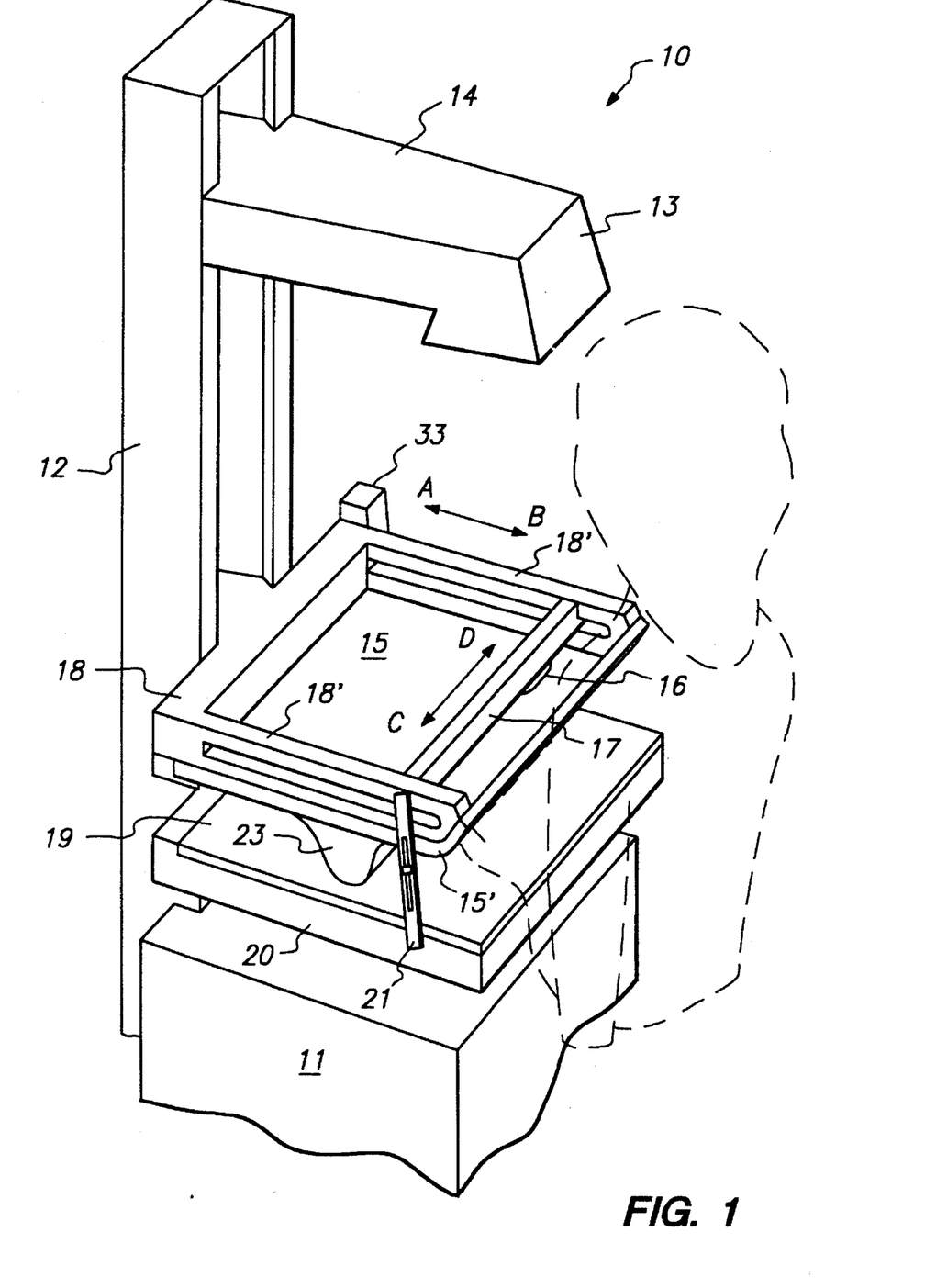
FIG. 1 is a perspective view of a first embodiment of the sonomammography apparatus of the present invention.
Figure 2:
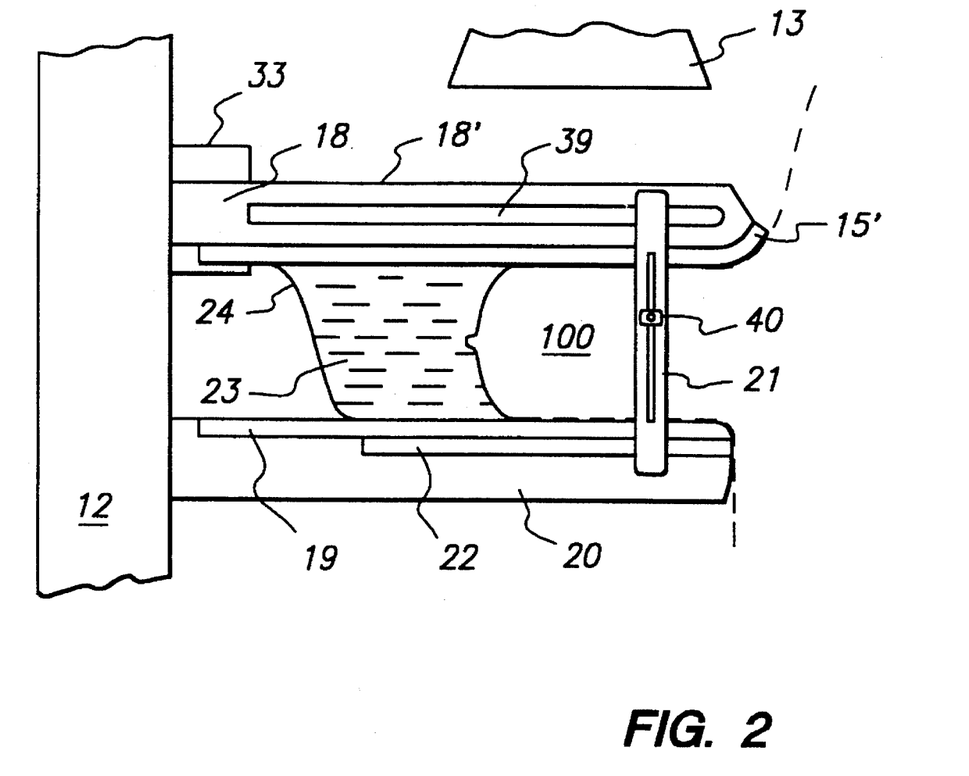
FIG. 2 is a partial elevation side view of the sonomammography apparatus of FIG. 1.

Referring to FIGS. 1 and 2, an illustrative embodiment of a first embodiment of sonomammography apparatus 10 constructed in accordance with the present invention is described. Sonomammography apparatus 10 comprises base 11, vertical column 12, X-ray tube 13 suspended from arm 14, compression plate 15, ultrasound transducer 16 supported from gantry 17, gantry support 18, diffraction grid 19, film holder 20 and biopsy needle guide 21.

The mammography components of sonomammography apparatus 10, that is, base 11, column 12, X-ray tube 13, arm 14, diffraction grid 19 and film holder 20 may include the features hereinafter described, but otherwise may be conventional. As in previously known mammography equipment, the vertical elevation of arm 14 in column 12 may be selectively and movably determined either manually or using a motorized arrangement which is per se known. X-ray film 22 is disposed beneath diffraction grid 19 in film holder 20 through a door in the endface of the film holder.

While the illustrative embodiments provided herein refer to mammography equipment that generates X-ray films, it will of course be understood by one familiar with radiology that digital (filmless) X-ray systems could be employed as well. It is sufficient for purposes of practicing the present invention that X-ray radiation emitted from an X-ray source pass through biological tissue and form an image in a receptor, whether an X-ray film or a digital X-ray receptor. Commercially available mammography equipment that may be augmented in accordance with the present invention includes, for example, the Contour system by Bennett X-Ray Technologies, Inc., Copiague, N.Y., the AVIVA system available from Kramex, Saddle Brook, N.J., and the LORAD DSM system, available from Lorad, Danbury, Conn.

In addition to the above-described components of sonomammography apparatus 10 that are common to previously known mammography systems, the apparatus of the present invention includes compression plate 15 and ultrasonic transducer 16 movably supported on gantry 17. As shown in FIGS. 1 and 2, compression plate 15 includes gel pad 23 disposed from the underside of the compression plate, for example, by polyethylene bag 24. Compression plate 15 may include fenestrations (not shown) for conducting biopsies of the patient's tissue. Gel pad 23 contacts the frontal area of the patient's breast, i.e., the nipple area, to ensure proper transmission of acoustic waves from transducer 16 to the distal-most portion of breast tissue 100 with a minimum of impedance mismatch. As seen in FIGS. 1 and 2, gel pad 23 and polyethylene bag 24 conform to the distal-most portion of the breast to minimize impedance mismatch and acoustic reflectance at the gel pad/breast interface. Accordingly, gel pad may comprise an agar gelatin and water composition or other suitable rheostatic material. For sanitary purposes, gel pad 23 and polyethylene bag 24 may be disposable, and therefore removably attached to compression plate 15.

In accordance with the first embodiment of the present invention, compression plate 15 comprises a high performance acoustically transparent ("sonolucent") and X-ray transparent ("radiolucent") film which is sufficiently rigid to serve as a compression plate. Suitable materials should have mechanical properties, for a 1 mil (25 micron) thickness, such as a tensile strength of about 24,000 psi, a dielectric strength of about 6000 AC volts/mil, and a volume resistivity of about $10^{12}$ ohm-cm at 200°. For further rigidity, compression plate 15 may include metal reinforcing bars 15' along its lateral endfaces.

Kapton™ manufactured by E.I. Du Pont de Nemours and Company, Wilmington, Del., is an ideal material for practicing the present invention, as it provides both the needed sonolucent/radiolucent qualities as well as the needed rigidity to provide satisfactorily as a compression plate. In particular, a 1 mil (25 micron) thickness of Kapton, when used as a compression plate, is expected to cause less than 3 dB transmission loss in acoustic energy, while providing a tensile strength equivalent to that of a 2 mm thick polycarbonate plate. In addition, Kapton is unaffected by exposure to X-ray radiation.

Referring still to FIGS. 1 and 2, ultrasonic transducer 16 may comprise a single piston, annular or phased array imaging device of conventional design. Such array devices may permit beam-focussing of ultrasonic energy to provide high resolution images of the internal structures of a patient's tissue. Ultrasound transducer 16 combines both transmit and receive functions that are switched, respectively, between transmitting and receiving operational modes at selected times by control circuitry.

Because the internal structure and operation of ultrasonic apparatus is per se known, the specific internal configuration of that apparatus forms no part of the present invention. Transducer 16 preferably operates in a range of about 2 to 15 MHz. More preferably, the signal produced by the transducer in the transmit mode is a 10 MHz burst having a 100% bandwidth. Transducer 16 may in addition be acoustically coupled to the upper surface of compression plate 15 using an appropriate coupling agent such as, for example, glycerol, or an additional thin gel pad disposed atop compression plate 15 (omitted for clarity from FIG. 1).

Figure 3:
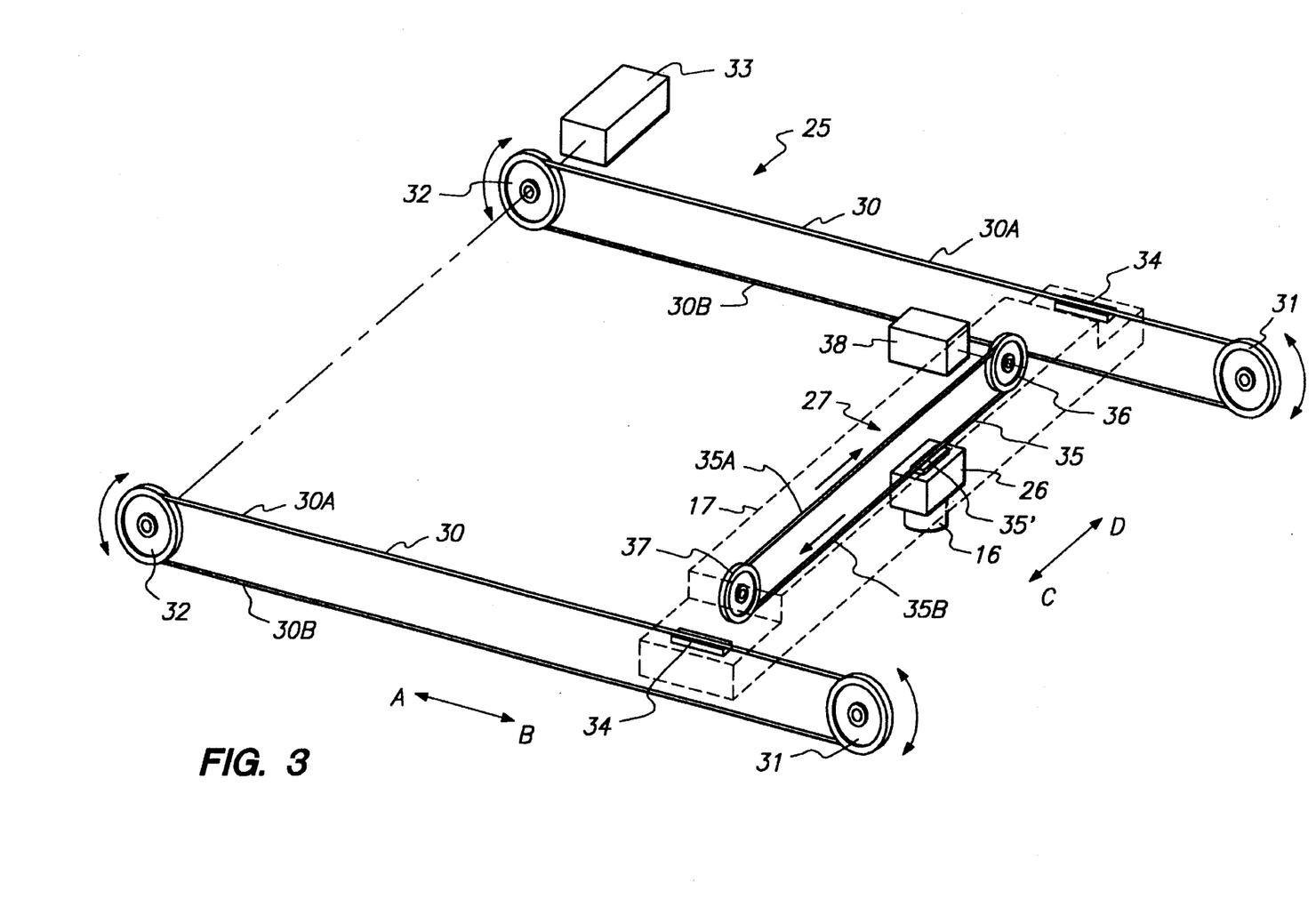
FIG. 3 is a schematic view of an illustrative embodiment of the drive means employed in the sonomammography apparatus of FIG. 1.

Referring to FIGS. 1–3, gantry support 18 is vertically positioned along column 12 using a motorized or manually adjustable mechanism. Gantry support 18 includes arms 18' disposed above the lateral edges of compression plate 15. Gantry support 18 movably supports gantry 17 for movement in distal and proximal directions "A" and "B", using a motorized track or cable arrangement 25. Gantry support 18 moves gantry 17 in precise increments in the distal and proximal directions. During X-ray exposure of the patient's tissue, gantry 17 is moved to a distal-most position in direction "A" so that it does not interfere with the mammogram exposure.

Gantry 17 (shown by dotted lines in FIG. 3) in turn comprises carriage 26 that supports ultrasonic transducer 16. Gantry 17 includes its own motorized drive means 27 for moving carriage 26 laterally in directions "C" and "D".

Illustrative embodiments of drive means 25 and 27 are described with respect to FIG. 3. Drive means 25 of gantry support arm 18 may comprise cables 30 that extend through arms 18' of gantry support 18. Cables 30 are captured on pulleys 31 and drive wheels 32 to form upper and lower flights 30A and 30B, respectively. Drive wheels 32 are synchronously driven by motor 33. Gantry 17 is fixedly connected to the upper flights of cables 30 at points 34, so that when the upper flights of cables 30 move in directions "A" and "B", gantry 17 translates in the corresponding direction. Motor 33 is of a type that enables exact positioning of gantry 17, for example, so that the gantry 17 can be moved in the proximal and distal directions in precise increments, such as 1 to 10 mm.

Still referring to FIG. 3, gantry 17 includes its own cable arrangement 27 for precisely positioning carriage 26 and transducer 16. In particular, in the illustrative embodiment shown, cable 35 runs on drive wheel 36 and pulley 37 to form upper and lower flights 35A and 35B, respectively. Carriage 26 is fixed to lower flight 35B of cable 35 at point 35' so that carriage 26 moves in directions "C" and "D" in response to movement of lower flight 35B. Motor 38, which is supported on gantry 17, enables precise control of carriage 26 and thus transducer 16.

Alternatively, a toothed belt and gear arrangement may be substituted for the cables, pulleys and drive wheels of the above-described illustrative embodiment. As further alternatives, drive means 25 and 27 may employ, for example, a conventional motorized track, a threaded block carried on a threaded drive rod controlled by an encoder and stepper motor, or any other suitable means.

It is to be understood that appropriately programmed control circuitry is provided for use with any of the foregoing drive means 25 and 27 so that the drive means pauses at predetermined locations during transit for a period sufficient to obtain an ultrasound image of the breast tissue at that location. In addition, gantry 17 and gantry support 18 may provide release mechanisms that enable transducer 16 to be manually positioned by the operator.

Referring again to FIG. 2, arm 18' of gantry support 18 includes slot 39, through which an extension of gantry 17 projects to engage biopsy needle guide 21. Thus, as gantry 17 moves in distal and proximal directions "A" and "B", biopsy needle guide 21 remains in alignment with ultrasonic transducer 16. Biopsy needle guide 21 includes a needle support element 40 having an aperture through which a biopsy needle may be inserted to perform an ultrasound image-guided biopsy of the patient's tissue. Needle support element 40 may be positioned at any desired position by the medical practitioner and then engaged with biopsy needle support 21 for performing image-guided biopsy.

Lateral alignment of the biopsy needle in accordance with this aspect of the present invention provides important psychological benefits to the patient. Since the biopsy needle is laterally inserted into the patient's breast, rather than through the upper surface, it produces no scarring on the upper surface of the breast. Accordingly, the patient will not be discouraged from wearing clothing, e.g., an evening gown which exposes the upper surface of the breasts, out of concern that unsightly scar tissue from a biopsy puncture will be visible.

Ultrasound transducer 16 generates an image corresponding to the internal structure of the tissue located in the plane perpendicular to transducer at each of the locations where carriage 26 stops during its transit across compression plate 15. The images or frames generated at each of these locations is stored on a microprocessor based workstation 41, such as shown in FIG. 4, for later postprocessing and manipulation.

Figure 4:
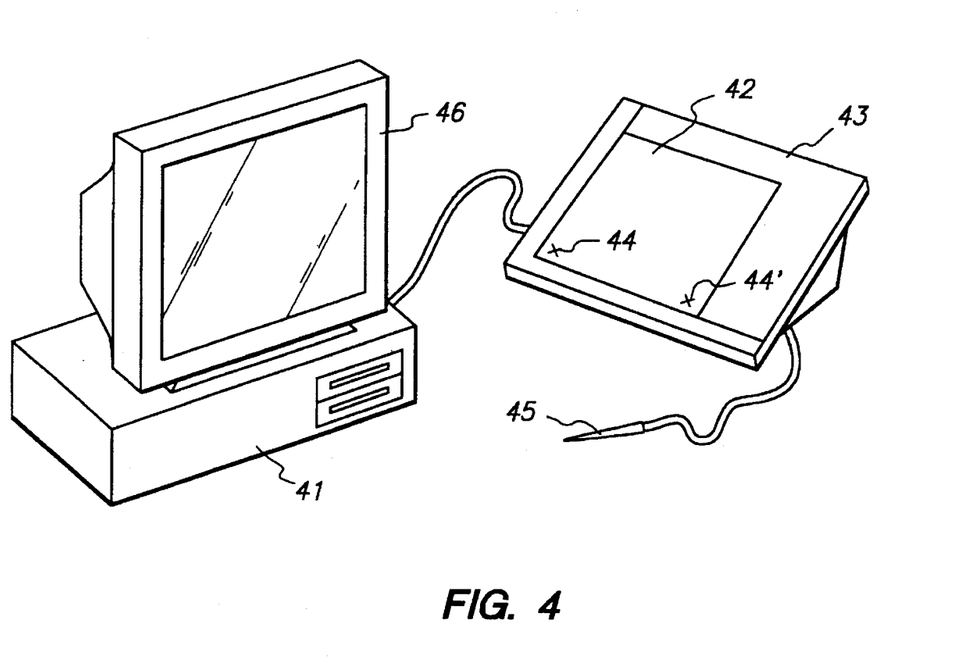
FIG. 4 is a perspective view of a workstation and digitizing tablet adapted for use with the present invention.

Referring now to FIG. 4, for an embodiment of the present invention for use with conventional mammography apparatus that generates an X-ray film, an X-ray film 42 is positioned on digitizing tablet 43 so that index marks 44 and 44' on the X-ray film coincide with positioning marks on digitizing tablet 43. Digitizing tablet 43 includes pen 45 and is connected to workstation 41 having monitor 46. Workstation 41 includes suitable software for interpreting movement of pen 45 with respect to digitizing tablet 43.

When X-ray film 42 is aligned on digitizing pad 43, pen 45 of the digitizing tablet enables the medical practitioner to display on monitor 46 the orthogonal ultrasound image corresponding to a location on X-ray film 42 by touching pen 45 to digitizing tablet 43. Thus, the position of the contact of pen 45 to digitizing tablet 43 automatically brings up the corresponding orthogonal ultrasound frame at that location, providing the medical practitioner with a holographic, i.e, three-dimensional, view of the internal structure of the tissue. Moreover, the precise geometric registration of the ultrasound image frames and the X-ray film provided by the present invention enables the medical practitioner to manipulate the ultrasound images, to perform, for example, digital subtraction, thereby enhancing breast lesion detection capability.

The PowerPC™ commercially available from Apple Computer, Cupertino, Calif., provides a suitable workstation for use as described above, while the HiSketch series of digitizing tablets, available from Kye International Corp., Ontario, Calif., provide suitable digitizing tablets for use in conjunction with the sonomammography apparatus of the present invention.

Figure 5:
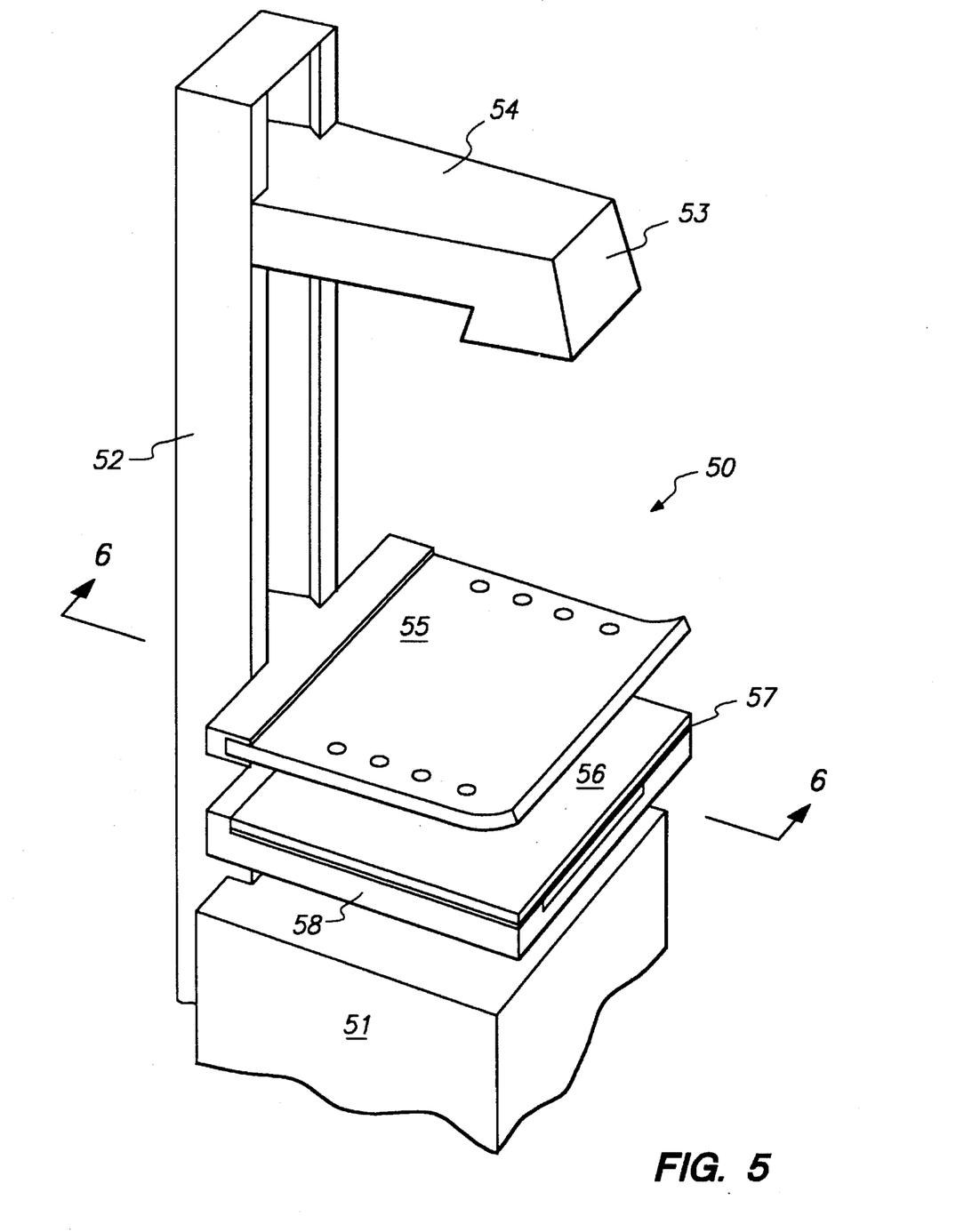
FIG. 5 is a perspective view of an alternative embodiment of the sonomammography apparatus of the present invention.
Figure 6:
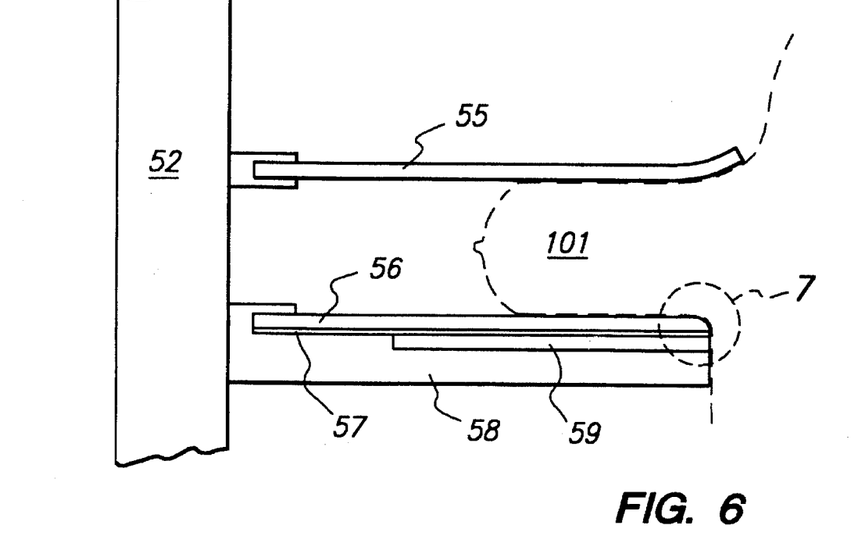
FIG. 6 is a cross-sectional view taken along view line 6—6 of FIG. 5.
Figure 7:
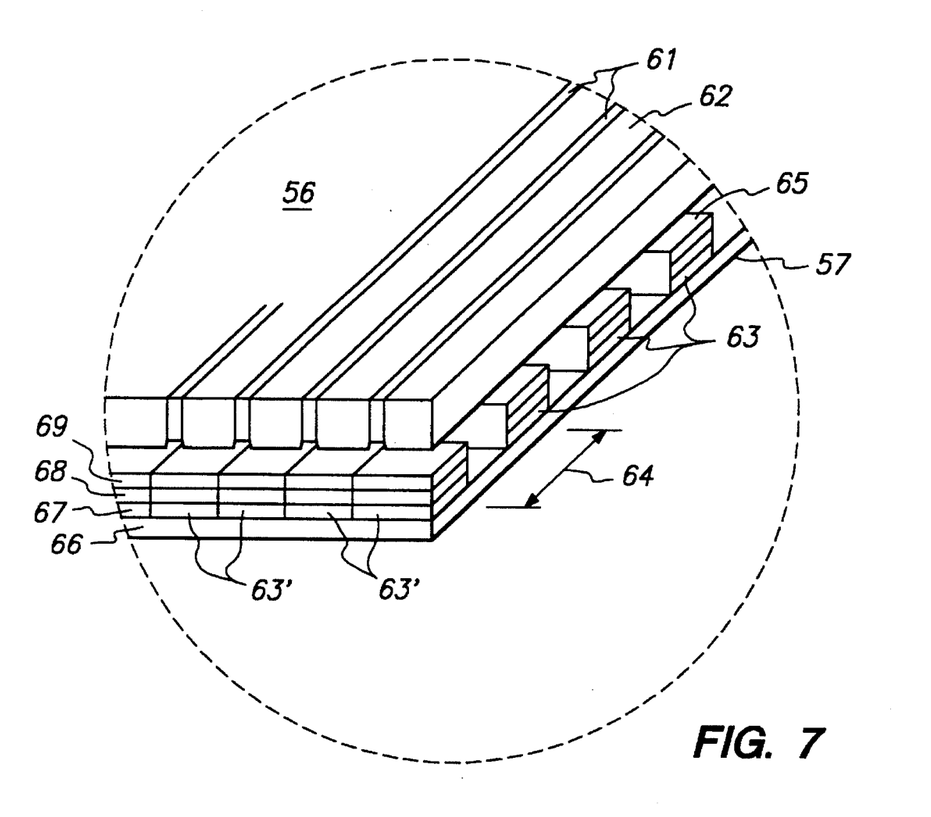
FIG. 7 is a perspective view of the diffraction grid and ultrasonic transducer apparatus of the present invention.

Referring now to FIGS. 5–7, an alternative embodiment of a sonomammography apparatus 50 constructed in accordance with the principles of the present invention is described. Sonomammography apparatus 50 includes base 51, upright vertical column 52, X-ray tube 53 supported on vertical movable arm 54, compression plate 55, diffraction grid 56, ultrasound transducer 57 and film holder 58. Components 50–54 may constitute the elements of a conventional mammography system as described hereinabove. X-ray sensitive film 59 is disposed in film holder 58 beneath ultrasound transducer 57.

Sonomammography apparatus 50 differs from apparatus 10 described hereinabove principally in that the sonolucent compression plate 15, transducer 16, gantry 17 and gantry support 18 are replaced by modified diffraction grid 56 and ultrasound transducer 57. Compression plate 55 may be fenestrated to enable the medical practitioner to perform ultrasound-image guided biopsies.

Referring now to FIG. 7, diffraction grid 56 comprises an array of an X-ray absorptive material 61, such as lead, having its interspaces filled with a non-absorptive material 62, such as aluminum or an organic material. This arrangement, which is conventional for mammography systems, permits those X-rays which are perpendicular to plane of diffraction grid 56 to pass through interspaces 62, while the array of lead lines 61 absorbs most of the diffuse radiation caused by scattering of the X-rays as they pass through the patient's tissue 101. Diffraction grid 56 differs from previously known devices, in that the lower surfaces of interspaces 62 extend below the lower surfaces of lead lines 61 by about 1 mm. The spaces between the extended interspaces thereby create air pockets that serve as an acoustic absorber between ultrasonic transducer 57 and lead lines 61.

Ultrasonic transducer 57 serves the same purpose as ultrasound transducer 16 of the embodiment of FIGS. 1–3, namely, to alternatively send and receive acoustic energy. Ultrasonic transducer 57 comprises a two-dimensional array of piezoelectric linear or phased arrays 63 spaced in parallel relation. Arrays 63 may have their axes aligned orthogonally with the lead lines of diffraction grid 56, as shown in FIG. 7, or may have their axes aligned with interspaces 62. Each of the arrays 63 comprises a multiplicity of ultrasonic transducers elements 63' that can be individually and sequentially activated. Spacing 64 between arrays 63, which may be for example 1 cm, determines the spacing between adjoining frames of the ultrasound images provided by transducer 57. This resolution, as well as elevational focussing, can be improved by providing suitable circuitry for focussing the acoustic energy emitted by multiple ultrasonic transducer elements 63', i.e., by activating elements in adjacent rows.

Each of ultrasonic transducer elements 63' is connected to an ultrasound controller circuit, described hereinafter, by a series of connecting wires (not shown in FIG. 7). The connecting wires are routed across the two-dimensional array so that they coincide with the rows of X-ray absorptive material in diffraction grid 56. By so arranging the connecting wires to ultrasonic transducer elements 63', the connecting wires will not create images on the X-ray film during exposure of that film.

Upper surfaces 65 of ultrasonic transducer elements 63' are acoustically coupled to interspaces 62 of diffraction grid 56 using a suitable coupling agent, for example, glycerol. Acoustic energy emitted by ultrasonic transducer elements 63' is transmitted through the interspaces of diffraction grid 56 and into tissue disposed between upper compression plate 55 and diffraction grid 56. A gel pad, such as that described above with respect to the embodiment of FIGS. 1–3 may be used in conjunction with compression plate 55 and diffraction grid 56 to reduce the acoustic impedance mismatch at the interface between the diffraction grid and the distal-most portion of the patient's breast tissue 101.

Referring still to FIG. 7, arrays 63 comprise a series of layers including a piezoelectric material, such as copolymers of vinylidene fluoride (VDF) and trifluoroethylene (TrFE), for example, available from Toray Industries, Kamakura, Japan. Use of such materials to form ultrasonic transducers is described in Ohigashi et al., "Piezoelectric and Ferroelectric Properties of P(VDF-TrFE) Copolymers And Their Application To Ultrasonic Transducers", page 189 et seq., in *MEDICAL APPLICATIONS OF PIEZOELECTRIC POLYMERS* (Galetti et al. editors), Gordon and Breach Science Publishers S.A. (1988), which is incorporated herein by reference. The inventor has determined that a layer of gold plated copolymer material of about 1 mil (25 microns) is practically transparent to X-ray (and ultrasound), the change in the received signal when the copolymer film is inserted between the X-ray source and the film being less than 1 dB.

As shown in FIG. 7, arrays 63 may form a phased array. An example of a integrated-silicon VDF-TrFE acoustic transducer array demonstrated for use diagnostic imaging is described in Ohigashi et al. above. Such arrays exhibit a low degree of array element cross-coupling, may be easily fabricated in high density, and provide excellent acoustic impedance matching to biological tissue.

Still referring to FIG. 7, ultrasonic transducer 57 comprises thin metal backing plate 66 covered piezoelectric film 67 of a suitable material described hereinabove, for example, a copolymer of VDF and TrFE. Piezoelectric film 67 is in turn covered by electrode element 68, and carries on its upper surface an inactive polymer layer 69. Connecting wires (not shown) are routed to the respective electrode elements of each of the ultrasonic transducer elements 63' so as to coincide with the lines of X-ray absorptive material in diffraction grid 56. Inactive polymer layer 69 is acoustically coupled to the lower ends of the interspace material of the diffraction grid using a suitable coupling agent as described hereinabove.

It will be recognized by one skilled in the art of ultrasonic transducer design that ultrasonic transducer elements 63' of ultrasonic transducer 57 can be fabricated to operate at a predetermined frequency by the selection of the thicknesses of components 66–69. Furthermore, it will be recognized that because the acoustic signals received by the arrays during receiver operation may include a strong reflection from the lower surface of the X-ray absorptive grid of diffraction grid 56 (i.e., very strong impedance mismatch), it may be necessary to filter the echo signals to eliminate this artifact. For example, echo signals obtained using a water path may be stored in the filtering circuitry and then subtracted from the echoes received by the ultrasonic transducer during actual operation.

In addition, it will be understood that by employing suitable circuitry for controlling activation of the ultrasonic transducer elements, only those transducer elements corresponding to a predetermined location may be activated. Thus, by employing a biopsy needle support, such as that shown in FIG. 1 with an appropriate mechanism for aligning the support with the ultrasonic transducer elements of interest, the medical practitioner may perform a biopsy guided by ultrasonic images, just as for the embodiment described in FIGS. 1–3.

Figure 8:
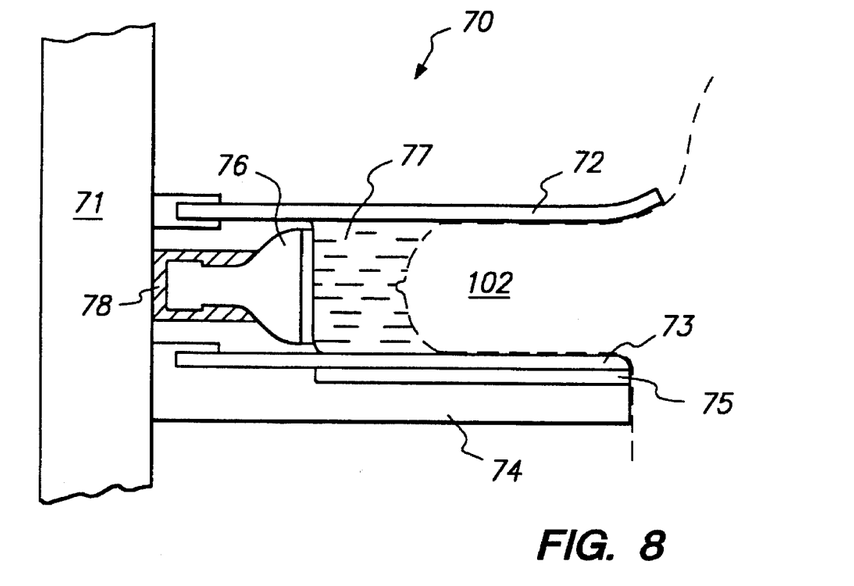
FIG. 8 is a cross-sectional view of another alternative embodiment of the present invention.

Referring now to FIG. 8, another alternative embodiment of the sonomammography apparatus of the present invention is described. Sonomammography apparatus 70 includes the basic elements of a mammography system as described hereinabove, including upright vertical column 71, compression plate 72, diffraction grid 73, film holder 74 and X-ray sensitive film 75, and ultrasound transducer 76. In this embodiment, compression plate 72 need not be sonolucent, since ultrasonic transducer 76 is positioned between the compression plate and the diffraction grid. Gel pad 77 affixed to compression plate 72 ensures acoustic coupling of ultrasound transducer 76 to the biological tissue 102.

Unlike the gantry of the embodiment of FIGS. 1–3, ultrasound transducer 76 is mounted on a horse-shoe-shaped gantry 78, so that the transducer follows a curved path as it translates along gantry 78. Ultrasound transducer 76 moves in small angular increments, for example, 1 to 3 degrees, as it traverses the length of gantry 78.

It will be recognized by one skilled in the art of ultrasonic transducer design that this third arrangement provides a greater depth for the acoustic energy to penetrate in comparison to embodiments described hereinabove. Consequently, it may be necessary to employ lower frequency transducers for this embodiment than would be used in the previously described embodiments. For most superficial lesions, however, it is expected that a high frequency transducer would still provide satisfactory performance.

Figure 9:
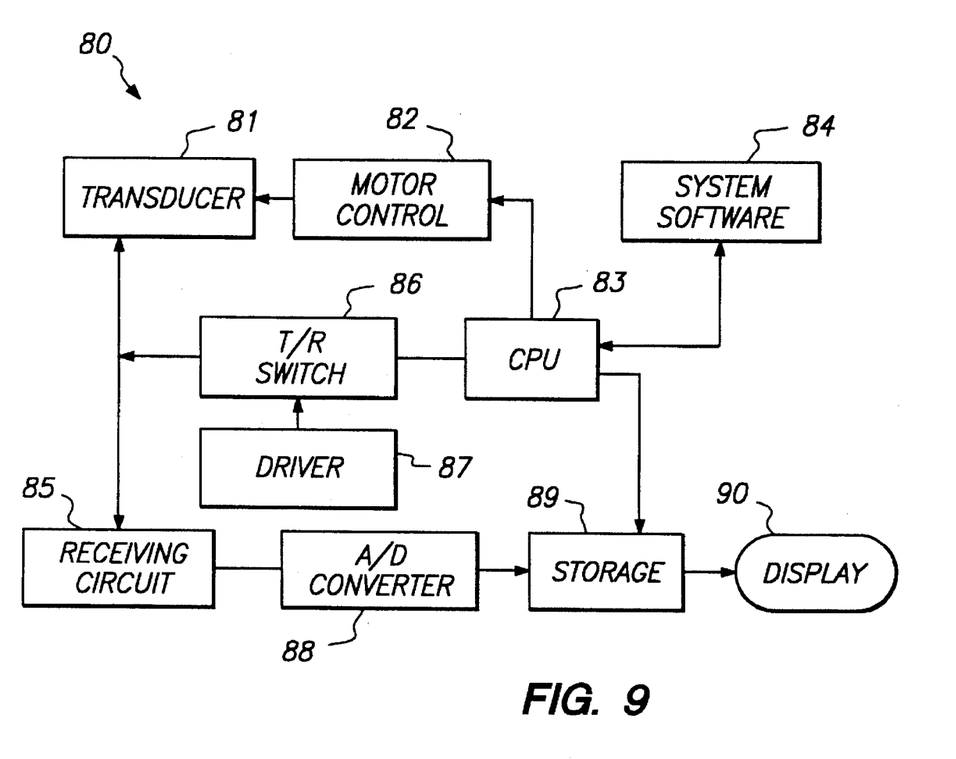
FIG. 9 is a block diagram of the elements of an ultrasonic imaging system in accordance with the present invention.

Referring now to FIG. 9, ultrasound circuit 80 for imaging a patient's tissue is described. Circuit 80 includes ultrasonic transducer 81, motor controller 82, microprocessor 83 run by system software 84, receiving circuit 85, transmit/receive switch 86, drive circuit 87, analog to digital converter 88, system storage 89 and display 90.

Transducer 81 is energized by drive circuit 87 to emit ultrasonic signals. Once the transducer has emitted acoustic energy for a suitable period, the transducer is switched to receiving mode. As transducer 81 responds to the echoes of the emitted signals, it generates electrical signals in receiving circuit 85.

Receiving circuit 85 preferably has a wide dynamic range, for example, 100 dB, to enable high contrast resolution. Since the receiving circuit records the transmitted pulse as well as the returning echoes, the first $T_0$ microseconds corresponding to the time-of-flight from the transducer surface to the tissue is ignored. Receiving circuit 85 also includes an automatic gain amplifier that can be adjusted to compensate for the attenuation of the returning signal. The received signal is therefore amplified and processed by receiving circuit 85 before being fed to analog-to-digital converter circuit 88. Analog-to-digital converter translates the analog electrical echo signals into digital signals, which are in turn stored in system storage device 89.

Microprocessor 83 monitors motor controller 82, which in turn controls the movement of the ultrasonic transducer (for example, movement of gantry 17 and gantry support 18 in the embodiment of FIGS. 1–3) and continuously computes the position of transducer 81. The digitized data corresponding to the gantry location at each ultrasound image location is stored in system storage 89 together with the ultrasound image at that location.

Alternatively, because the digitized data collected after each pulse is stored in system storage device 89 in a consecutive manner, and the propagation path for either electronic or mechanical steering can be predetermined, the orientation and position of transducer 81 may be directly correlated with the location of the digital data stored in system storage 89.

It is known to use ultrasonic signals for the assessment of tissue vasculature by estimating the frequency or temporal shift due to blood flow through the imaged tissue. Such systems, which are based on the Doppler principle, are described in Baker, "Pulse Ultrasound Doppler Blood Flow Sensing", IEEE Transactions on Sonics and Ultrasonics, Vol. SU-17, No. 3 (1970). Data related to blood flow may also therefore be acquired using ultrasound transducer 81, which data may be processed and stored in system storage 89 together with the echo data.

In addition, because blood flow creates a speckle effect in the ultrasound image, it may be desirable to transmit several pulses at each imaging location and then use standard noise reduction techniques to average out the speckle effect caused by blood flow. Also, the variation in speckle due to the motion of the transducer enables several consecutive acquisitions of the return echo to be averaged to reduce the speckle. Digital subtraction of the data received from a water path and most probably due to reverberations could also be subtracted from the digitized data to improve the ultrasound image.

For an embodiment of the present invention such as that shown in FIGS. 5–7, microprocessor 83 may control the sequential operation of the individual ultrasonic transducer elements 63' of the two-dimensional ultrasonic transducer 57. The location of the ultrasound images in storage system 89 may be used to correlate those images with specific locations in the phased array, as described above.

System software 84, which may reside in a conventional microprocessor based workstation, enables data stored in storage device 89 to be manipulated so that holographic views may be generated and viewed from different angles. In addition, the software may enable viewing of a particular region of interest determined relative to the radio-opaque lines (not shown in FIGS. 1 or 5) provided on the compression plate or in accordance with the position of the pen of the digitizing tablet, as described above with respect to FIG. 4. Images are displayed on display device 90.

Set-up and operation of the sonomammography apparatus of the present invention is straight forward, and can be accomplished by a single operator. The medical practitioner or operator positions the breast for mammographic studies in conventional fashion. Following (or before) the X-ray exposure, the ultrasound transducer is activated to image the breast tissue at discrete locations, with the ultrasound images being stored for review on the workstation.

One potential way of viewing the stored ultrasound image data is similar to conventional mammography. Since cross-sectional views of the entire breast are stored, it is possible to sum each propagation line and obtain a two-dimensional projection map of the breast attenuation. Such an approach is expected to be useful in breast cancer screening. Alternatively, a three dimensional representation of a region of interest may be displayed, which may be especially useful in analyzing the Doppler or vasculature data. An alternative presentation of the data might consist of a loop of consecutive frames.

The acoustic backscattering of tissue is a function of density and compressibility. The inventor has further determined that a non-linear relationship with respect to compression exists for malignant tissue. Those results suggest that tumor detection may be enhanced by compression of the breast tissue and the use of digital subtraction techniques to isolate suspicious lesions.

Likewise, the knowledge of the relative position of a tissue segment in both breasts allows the use of digital subtraction techniques using the digitized ultrasound images to isolate suspicious lesions. For example, the ultrasound image frames from similar planes in both breasts may be digitally subtracted and the difference in intensities summed. Based on a predetermined threshold, only images that are deemed to substantially different, using that test, are presented for review by the medical practitioner.

The present invention further includes a method of obtaining an X-ray image and a geometrically registered ultrasound image of biological tissue, as is apparent from the foregoing apparatus descriptions. That method comprises the steps of:

(a) immobilizing the biological tissue with respect to a reference point;

(b) exposing the biological tissue to X-rays to generate an X-ray film of the internal structure of the biological tissue;

(c) without any intervening movement of the biological tissue with respect to the reference point, coupling an ultrasonic transducer to the biological tissue to generate a plurality of the ultrasound images of the biological tissue; and (d) precisely correlating the plurality of ultrasound images with predetermined locations on the X-ray film.

It will of course be understood that steps (b) and (c) of exposing the tissue to X-ray radiation and conducting the ultrasound scanning may be readily interchanged as needed in a particular application.

In addition, the method in accordance with the present invention may also include the steps of processing, storing and manipulating the ultrasound images to enhance the diagnostic capabilities of the stored images, using, for example, noise filtering or digital subtraction techniques.

It will be understood that the foregoing is merely illustrative of the apparatus and methods of the present invention, and that various modifications can be made by those skilled in the art without departing from the scope and spirit of the invention.

What is claimed is:

1. In apparatus for obtaining radiological images of biological tissue by passing X-ray radiation through a biological tissue to form an image in a receptor, the apparatus comprising an X-ray source for emitting X-ray radiation, an upper compression surface and a lower compression surface adapted for immobilizing the biological tissue therebetween, and a receptor disposed beneath the lower compression surface, the X-ray source disposed above the upper compression surface so that X-ray radiation emitted from the source passes through the biological tissue and is received by the receptor, the improvement comprising:

a compression plate that is radiolucent and sonolucent, the compression plate having an upper surface and a lower surface, the lower surface forming the upper compression surface;

an ultrasonic transducer disposed above the compression plate;

drive means for moving the ultrasonic transducer through a predetermined path across the upper surface of the compression plate while the biological tissue remains immobilized between the upper and lower compression surfaces, so that the ultrasonic transducer generates a plurality of ultrasound images of the biological tissue that are in geometric registration with the image formed in the receptor.

2. The apparatus as defined in claim 1 wherein the compression plate comprises a material having the properties of Kapton.

3. The apparatus as defined in claim 1 further comprising a gel pad for acoustically coupling a portion of the biological tissue to the ultrasonic transducer.

4. The apparatus as defined in claim 1 wherein the drive means further comprises:

a gantry support;

a gantry movably engaged with the gantry support for movement in the distal and proximal directions;

a carriage movably engaged with the gantry for lateral movement.

5. The apparatus as defined in claim 4 wherein the drive means further comprises:

a first motorized cable arrangement for driving the gantry along the gantry support;

a second motorized cable arrangement for driving the carriage along the gantry; and circuitry for controlling operation of the first and second motorized cable arrangements.

6. The apparatus as defined in claim 1 further comprising:

a biopsy instrument support;

means for aligning the biopsy instrument support with the ultrasonic transducer so that a medical practitioner may perform a biopsy guided by the plurality of ultrasonic images.

7. In apparatus for obtaining radiological images of biological tissue by passing X-ray radiation through a biological tissue to form an image in a receptor, the apparatus comprising an X-ray source for emitting X-ray radiation, an upper compression surface and a lower compression surface adapted for immobilizing the biological tissue therebetween, and a receptor disposed beneath the lower compression surface, the X-ray source disposed above the upper compression surface so that X-ray radiation emitted from the source passes through the biological tissue and is received by the receptor, the improvement comprising:

an ultrasonic transducer disposed beneath the lower compression surface and acoustically coupled thereto for transmitting acoustic energy to the biological tissue, the ultrasonic transducer being radiolucent;

control circuitry for activating the ultrasonic transducer to generate a plurality of ultrasound images of the biological tissue while the biological tissue remains immobilized between the upper and lower compression surfaces, the plurality of ultrasound images of the biological tissue being in geometric registration with the image formed in the receptor.

8. The apparatus as defined in claim 7 wherein the ultrasonic transducer comprises a multiplicity of piezoelectric transducer elements.

9. The apparatus as defined in claim 8 wherein the control circuitry further comprises circuitry for activating predetermined ones of the multiplicity of piezoelectric transducer elements to provide beam forming and elevational focussing of the acoustic energy.

10. The apparatus as defined in claim 7 further comprising a gel pad for acoustically coupling a portion of the biological tissue to the ultrasonic transducer.

11. The apparatus as defined in claim 8 wherein the control circuitry comprises circuitry for activating a predetermined plurality of the multiplicity of piezoelectric elements to generate an ultrasonic image at a predetermined location, the apparatus further comprising:

a biopsy instrument support;

means for aligning the biopsy instrument support with the predetermined plurality of piezoelectric elements so that a medical practitioner may perform a biopsy guided by the ultrasonic image at the predetermined location.

12. Apparatus for generating a plurality of ultrasound images of a biological tissue, the apparatus for use with an X-ray system that forms an image of the biological tissue in a receptor, so that when the apparatus is used with the X-ray system the plurality of ultrasound images of the biological tissue are in geometric registration with the image formed in the receptor, the apparatus comprising:

a compression plate that is radiolucent and sonolucent, the compression plate having first and second surfaces, the first surface forming a compression surface against which the biological tissue is immobilized;

an ultrasonic transducer disposed adjacent the second surface;

drive means for moving the ultrasonic transducer through a predetermined path across the second surface while the biological tissue remains immobilized against the compression surface.

13. The apparatus as defined in claim 12 wherein the compression plate comprises a material having the properties of Kapton.

14. The apparatus as defined in claim 12 further comprising a gel pad for acoustically coupling a portion of the biological tissue to the ultrasonic transducer.

15. The apparatus as defined in claim 12 wherein the drive means further comprises:

a gantry support;

a gantry movably engaged with the gantry support for movement in the distal and proximal directions;

a carriage movably engaged with the gantry for lateral movement.

16. The apparatus as defined in claim 12 wherein the drive means further comprises:

a first motorized cable arrangement for driving the gantry along the gantry support;

a second motorized cable arrangement for driving the carriage along the gantry; and circuitry for controlling operation of the first and second motorized cable arrangements.

17. The apparatus as defined in claim 12 further comprising:

a biopsy instrument support;

means for aligning the biopsy instrument support with the ultrasonic transducer so that a medical practitioner may perform a biopsy guided by the plurality of ultrasonic images.

18. Apparatus for generating a plurality of ultrasound images of a biological tissue, the apparatus for use with an X-ray system that forms an image of the biological tissue in a receptor, so that when the apparatus is used with the X-ray system the plurality of ultrasound images of the biological tissue are in geometric registration with the image formed in the receptor, the apparatus comprising:

a compression surface against which the biological tissue is immobilized, the compression surface being radiolucent;

an ultrasonic transducer disposed adjacent to the compression surface and acoustically coupled thereto for transmitting acoustic energy to the biological tissue;

control circuitry for activating the ultrasonic transducer to generate a plurality of ultrasound images of the biological tissue while the biological tissue remains immobilized against the compression surface.

19. The apparatus as defined in claim 18 wherein the ultrasonic transducer comprises a multiplicity of piezoelectric transducer elements.

20. The apparatus as defined in claim 19 wherein the control circuitry further comprises circuitry for activating predetermined ones of the multiplicity of piezoelectric transducer elements to provide beam forming and elevational focussing of the acoustic energy.

21. The apparatus as defined in claim 19 wherein the control circuitry comprises circuitry for activating a predetermined plurality of the multiplicity of piezoelectric elements to generate an ultrasonic image at a predetermined location, the apparatus further comprising:

a biopsy instrument support;

means for aligning the biopsy instrument support with the predetermined plurality of piezoelectric elements so that a medical practitioner may perform a biopsy guided by the ultrasonic image at the predetermined location.

22. The apparatus as defined in claim 18 further comprising a gel pad for acoustically coupling a portion of the biological tissue to the ultrasonic transducer.

23. The apparatus as defined in claim 18 wherein the transducer is radiolucent.

* * * * *